Figure 1:
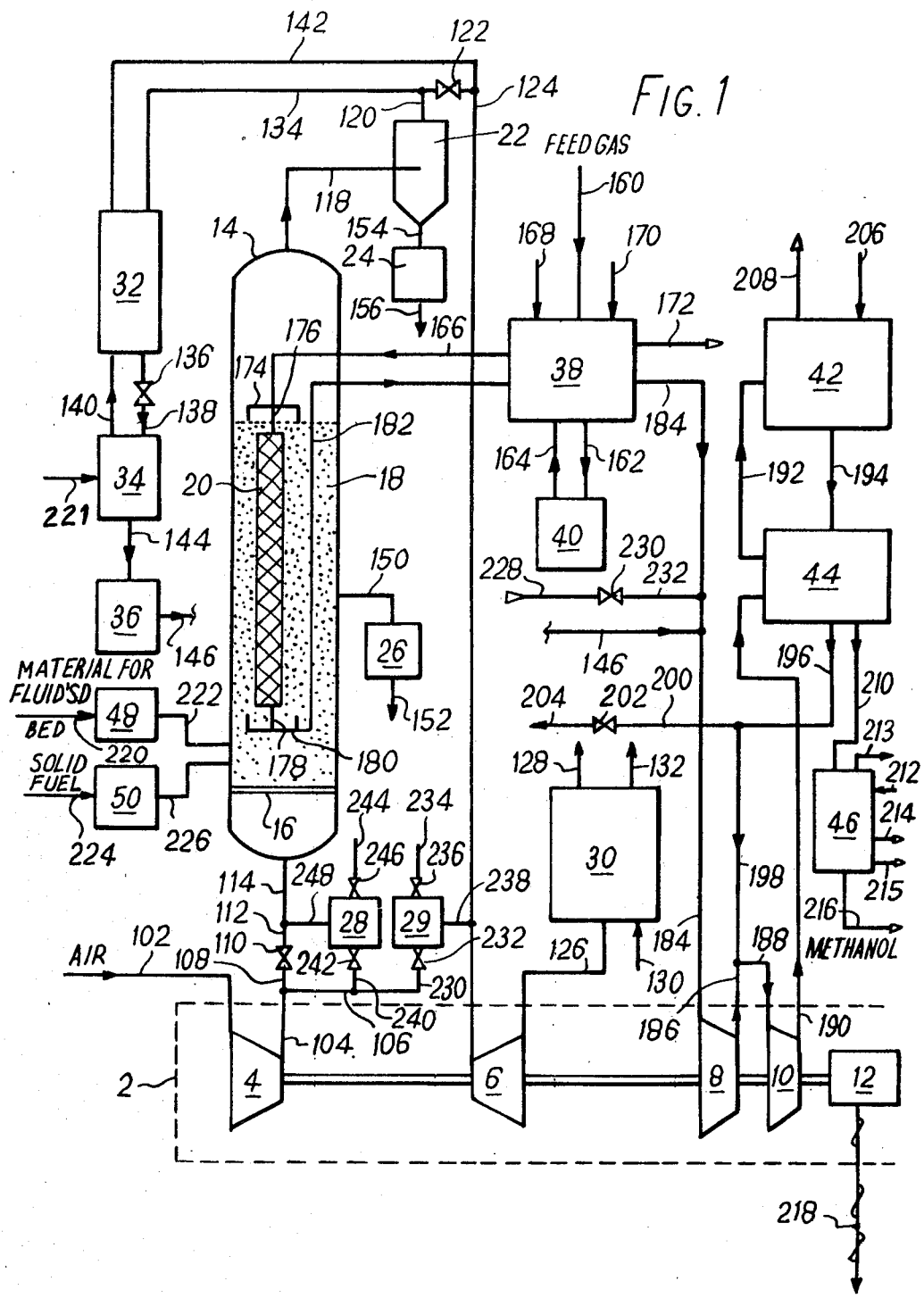

United States Patent [19]

Cummings

[11] 4,395,495
[45] Jul. 26, 1983

[54] PRODUCTION OF METHANOL

[75] Inventor: Donald R. Cummings, Cheltenham, England

[73] Assignee: D.U.T. Pty Ltd., Sydney, Australia

[21] Appl. No.: 171,962

[22] Filed: Jul. 24, 1980

[30] Foreign Application Priority Data

Aug. 2, 1979 [GB] United Kingdom ............... 7926932

[51] Int. Cl.³ .............................................. C07C 29/15
[52] U.S. Cl. .................................. 518/704; 518/705; 518/728; 252/373
[58] Field of Search ................ 252/373; 518/704, 728, 518/705

[56] References Cited

U.S. PATENT DOCUMENTS

| Re. 26,990 | 11/1970 | Bongiorno | 252/373 |
|---|---|---|---|
| 2,132,533 | 10/1938 | Koppers | 252/373 |
| 2,383,715 | 8/1945 | DeJahn | 252/373 |
| 2,614,915 | 10/1952 | Hirsch | 252/373 X |
| 2,821,465 | 1/1958 | Garbo | 252/373 X |
| 3,597,465 | 8/1971 | Karafian et al. | 518/704 X |
| 3,920,717 | 11/1975 | Marion | 252/373 |

FOREIGN PATENT DOCUMENTS 2815985 10/1978 Fed. Rep. of Germany.

OTHER PUBLICATIONS

Hoy et al., pp. 59–77 of Pre–Print (1970), vol. 14, No. 2 of the American Chemical Society, Div. of Fuel Chemistry.

Primary Examiner—Bernard Helfin
Attorney, Agent, or Firm—Fred A. Keire

[57] ABSTRACT

In the production of methanol from a methane-containing gaseous feedstock such as natural gas by steam reforming the gas and treating the reformate to produce methanol by inter-reaction of the hydrogen and oxides of carbon in the reformate, the use of part of the feedstock to fire the reformer is avoided by immersing the reformer reactor tubes in a fluidized bed heated by the combustion of a low grade, solid, fossil-based fuel such as coal, lignite, oil shale or asphaltic residues from oil refining. By pressurizing the fluidized bed, all the power requirements of the process can be obtained by expansion of the flue gas, which can also provide the $CO_2$ balance for the methanol synthesis, and a compressor can be omitted.

12 Claims, 3 Drawing Figures

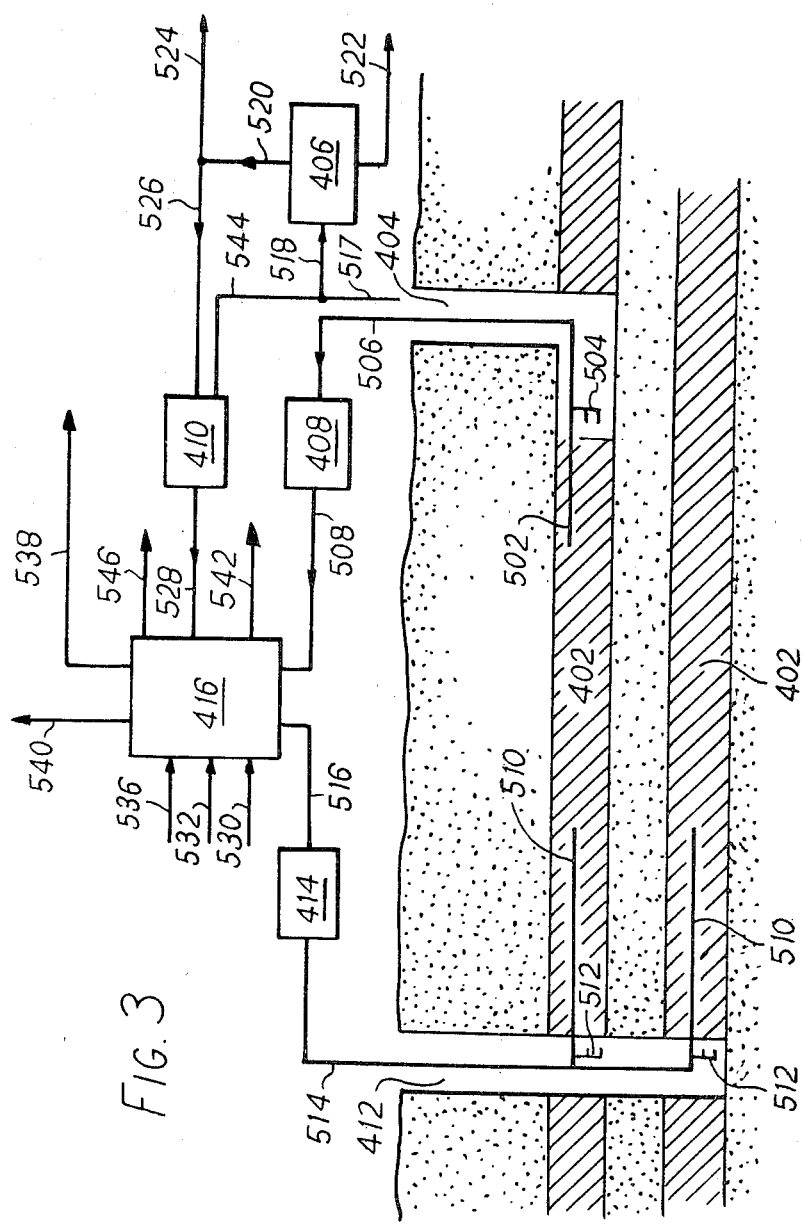

PRODUCTION OF METHANOL

This invention relates to the production of methanol from a gas, such as natural gas, which contains methane as a principal component.

Natural gas is frequently found in locations which are distant from industrialised communities and transport is a problem. At present, transport is effected by pumping the gas through a pipeline or by liquefying the gas and then transporting it by pipeline or by tanker. An attractive alternative, however, would be to convert the gas to methanol since this is easier and safer to handle and transport.

Another factor which favours examination of the practicality of converting natural gas to methanol is that whereas natural gas cannot readily be employed as a transport fuel, the use of methanol for this purpose is well recognised. Thus, providing methanol from natural gas, of which there are large reserves, would ease the current total dependence of the transport industry on the diminishing reserves of oil.

It is known that natural gas may be converted to methanol by steam reforming the natural gas to produce a gaseous reformate containing hydrogen and oxides of carbon and forming methanol from this reformate by reaction of the oxides of carbon with the hydrogen, e.g. in accordance with the following simplified equations:

Reforming $$CH_4 + H_2O \rightleftharpoons CO + 3H_2 \qquad (1)$$

$$CH_4 + 2H_2O \rightleftharpoons CO_2 + 4H_2 \qquad (2)$$

Methanol Production $$CO + 2H_2 \rightleftharpoons CH_3OH \qquad (3)$$

$$CO_2 + 3H_2 \rightleftharpoons CH_3OH + H_2O \qquad (4)$$

However, the reforming reaction is endothermic and is conducted at elevated temperatures, e.g. 800° C. to 900° C., and the methanol production step requires a higher pressure than the steam reforming step. Thus both heat for the reforming and energy for gas compression are required. In existing processes, these heat and energy requirements are supplied by combustion of a portion of the natural gas. This is because the use of a premium fuel such as natural gas is regarded as essential for the achievement of the critical degree of temperature control necessary for the practical operation of the reforming process and as the natural gas is already available as the chemical feedstock it is the natural first choice for the fuel. The overall efficiency of the production of the methanol from the natural gas, therefore, cannot readily exceed about 68% and this shortcoming has been the major factor in preventing development of this process as an alternative to pipelining the natural gas or transporting it as LNG and using it ultimately as a gaseous fuel. It has also been recognised for over a decade as constituting a serious disadvantage of the natural gas route to methanol and thus although the potential benefits of providing methanol from natural gas have been recognised for many years and have received particular attention and publicity since the late 1960s, in fact the process has in general only been employed for the production of methanol for chemical purposes.

Many proposals have been made for increasing the efficiency of the utilisation of the gas in the production of methanol. However, even though since 1973, or even earlier, the premium value of natural gas has been clearly established, and for upwards of a decade major studies have been undertaken to determine the optimum manner in which to develop gas resources in the context of known regional reserves of gas and other fuels, and in specific instances to consider the production of methanol from gas and proximate solid fuel reserves, to date these proposals have been directed at improvements in heat recovery despite the limited increase in efficiency that can be attained thereby; and although for many years there has been a major incentive to use low grade fuels in place of natural gas wherever possible, hitherto no practical proposal has been published for a process for producing methanol from natural gas wherein an alternate lower grade fuel is used to heat and power the plant.

The present invention provides a practicable route to methanol from natural gas or other methane-containing gas wherein the heat and energy requirements are supplied by the combustion of an alternate low grade fuel.

According to the present invention, there is provided a method of producing methanol from a methane-containing gas by the steps of (a) steam reforming said gas at elevated temperature to form a reformate containing hydrogen and oxides of carbon and (b) forming methanol from the reformate by reaction of the hydrogen with the oxides of carbon, and wherein the step of reforming the gas is effected in the presence of a catalyst within a reactor vessel and heat for the reaction is provided by at least partly immersing said reactor vessel in a heated fluidised bed of finely divided solid and at least a part, and preferably all, of the heat is provided by the combustion of a solid, fossil-based fuel.

For economic reasons it is preferred that the gas contains at least 40% by volume of methane and preferably more but gases containing less methane can be used. The balance, if any, will depend on the source of the gas but may include, for example, one or a mixture of the following: inert gases e.g. argon, nitrogen and helium, hydrogen, oxides of carbon, and hydrocarbons containing more than one carbon atom, e.g. ethane, propane, ethylene and propylene. Examples of such gases are natural gas, gas associated with crude oil recovery (known as associated gas), mine drainage gas, gas obtained from the biodegradation of organic matter, gas produced during the processing of crude oil or as a by-product in the production of synthetic oil, e.g. from coal, and purge gas from the production of methanol from methane-containing synthesis gas produced by the gasification of a solid fuel or oil. However, the process is particularly suitable for the processing of natural gas and mine drainage gas. Typically, such gases contain at least 70% methane, by volume.

By a solid fossil-based fuel is meant a fossil-based fuel which is normally solid at room temperatures. Examples are coal, lignite, peat, oil shale and oil-derived solid residues such as, for example, vacuum distillation residues, deasphalter residues and petroleum derived coke.

In the steam reforming step, the methane is reacted with steam in the presence of a catalyst to form hydrogen and oxides of carbon, e.g. in accordance with idealised equations (1) and (2) above. The conditions and catalysts appropriate for this steam reforming step are well known and generally include temperatures in the range 700°–1000° C., preferably 800°–900° C., and pressures in the range 100–600 psig, preferably 200 to 300 psig. The steam: methane ratio is generally 1:1–6:1, preferably about 4:1.

The process is preferably operated to achieve as high a conversion as possible and conversions of a high as 90% or higher, e.g. 95% to 98% may be achieved.

The reaction is preferably effected by passing the gaseous mixture through one or more heated tubes containing the catalyst. The manner of providing the heat is described below.

The reformate recovered from the reformer, and which will contain hydrogen, oxides of carbon, inert gases and unreacted methane, is then subjected to conditions under which the hydrogen reacts with the oxides of carbon e.g. in accordance with idealised equations (3) and (4). The conditions and apparatus appropriate for such methanol synthesis are well known and generally include temperatures in the range of 200° to 300° C. and pressures in the range 40–300 bar, preferably 65–100 bar.

It is preferred for the feed to the methanol synthesis reaction to include added carbon dioxide since this increases the amount of methanol that can be produced per mole of methane. The carbon dioxide may be added to the reformer feedstock but preferably it is added to the reformate prior to the methanol synthesis reaction. In the absence of carbon dioxide, the overall reaction for the production of methanol from methane by steam reforming can be represented as $$CH_4 + H_2O \rightleftharpoons CH_3OH + H_2.$$

In the presence of carbon dioxide, however, the reaction becomes $$CH_4 + \tfrac{1}{3}CO_2 + \tfrac{5}{3}H_2O \rightleftharpoons 4/3 CH_3OH.$$

The methanol synthesis may be effected in any suitable apparatus. As the temperature preferred for the methanol synthesis is substantially below that of the reforming step, in general it is necessary to cool the reformate prior to contacting it with the methanol synthesis gas. However, in accordance with Le Châtelier's principle, methanol production is favoured by high pressures and the pressures preferred for the methanol synthesis will normally be higher than those preferred for the reforming step in which case it will be necessary to compress the reformate.

In general, the art has found it expedient to operate the methanol synthesis at a relatively low conversion, e.g. 10 to 20%, and it is conventional to recycle the unreacted gases after treatment to remove the methanol e.g. by condensation and/or scrubbing. Because of the pressure drop through the reactor, it is necessary to recompress the recycle stream and because of the low conversion this recycle stream forms a large proportion of the total feed to the methanol synthesis reactor. To prevent the build-up of non-reactants in the reactor, a purge stream of appropriate size is usually bled from the recycle stream and may be employed as a fuel or a process gas.

The crude methanol recovered from the product stream from the methanol synthesis reactor may be purified in conventional manner.

In accordance with the invention, the heat required for the reforming step is provided by at least partly immersing the reformer reactor vessel, which may comprise a single catalyst-packed tube but more usually a plurality of catalyst packed tubes arranged in parallel with reference to the flow of process gas, in a fluidised bed of finely divided solid which is heated by the combustion of a solid fossil-based fuel. Such fluidised bed combustors have been known for decades and the nature and operation thereof are well publicised and understood.

An important aspect of the present invention, however, is the realisation that by employing a fluidised bed combustor to provide the heat to the reformer tubes, the problems hitherto associated with using a solid fuel, and in particular the problems of controlling the distribution of heat to the reformer reactor walls and avoiding the build up of deposits on the reactor walls, can be overcome and it is now possible to avoid using the valuable reformer feedstock for this purpose. In fact, not only can a sufficiently uniform heat transfer to the walls of the reactor tube be achieved, but temperature control can be improved over that obtainable using the premium gaseous fuel in a conventional radiant heat furnace.

Other advantages also accrue from the use of a fluidised bed combustor; in particular, elimination of the need to ensure an exact distribution of feed to each reformer tube, higher heat transfer rates with consequent reduction in the temperature of the flue gas leaving the reformer tube zone, lower temperature differences between heat source and tube wall, greater freedom in the shape and orientation of the reactor tubes, more compact arrangement of tubes and consequential reduction in overall apparatus size and refractory requirements, lower combustion flame temperature with consequential reduction in concentration of oxides of nitrogen in the flue gas; possibility of upward or downward flow of reaction mixture through the reactor tubes and, with the former, of using fluidised catalyst beds in the tubes, and superior turn down and flexibility of process control.

A particular advantage of the process of the invention, however, is that the fluidised bed may be under superatmospheric pressure and thus the pressure drop across the reformer reactor tube walls may be reduced or eliminated thereby permitting extended tube life, higher operating temperatures, use of thinner tube walls, use of lower grade tube material, higher pressures in the reformer tubes or a combination of two or more of these possibilities.

It has recently been proposed to form reformer reactor tube walls of ceramic materials in order to permit higher operating temperatures. Having the fluidised bed under superatmospheric pressure permits the placing of such tubes under compression, in which mode they offer better performance.

Yet another advantage of having the fluidised bed under pressure is that the furnaces will be basically totally enclosed and the design is therefore more suited to flame proof or generally hazardous areas than a conventional furnace.

The fluidised bed furnace in addition to being more compact will also contain much less refractory than, and need not have flat wall refractory as in, a conventional furnace. The fluidised bed furnace will therefore be more suited to transportation or installation in moving and floating plants such as may be required for the treatment of off-shore gases.

A very important advantage of having the fluidised bed at superatmospheric pressure is that energy in the flue gas from the combustor may be recovered by expanding the gas through an expansion engine such as a turbine which may be employed for example to drive a generator and/or to provide part or all of the compression energy requirements of the process, e.g. to compress the gaseous oxidant e.g. air to the combustor and/or to compress the reformate to the higher pressure required for the methanol production step and/or to recompress any recycle streams in the system e.g. unreacted or partially reacted reformate being recycled to the methanol production step. The extraction of energy directly in this fashion is more efficient than the conventional raising of high pressure superheated steam and the use of this steam in driving the process compressors or generating electricity.

It is desirable to operate the fluid bed combustor with excess air, preferably in the range 10 to 100% and most preferably in the range of 20% to 50% in excess of stoichiometric. It is also possible to operate the combustor with a deficiency of air with provision for burning off combustible gases by the addition of air after the fluid bed combustor.

By suitable choice of the pressure in the combustor and the amount of excess air supplied to the combustor, all the compression energy requirements of the process can be satisfied from the energy generated by the turbine.

As indicated above, improvements in the possible yield of methanol per mole of methane consumed may be achieved by injecting carbon dioxide into the gas mixture before reforming and/or before the methanol synthesis step. In accordance with another preferred embodiment of the invention, at least a part and preferably all of the carbon dioxide is provided from the flue gas from the fluidised bed combustor. The recovery of the carbon dioxide from the flue gas is facilitated by operating the combustor at superatmospheric pressure. Suitably, a part of the flue gas, generally up to about 25% thereof, is removed from the main portion of the flue gas, treated to recover carbon dioxide therefrom, and thereafter recombined with the main portion of the flue gas prior to expansion of the latter through a turbine to recover energy therefrom. In one embodiment, the carbon dioxide is recovered by washing in a scrubber and the scrubbed gas is then preferably reheated, e.g. by heat exchange with the gas being fed to the scrubber, prior to recombination with the main portion of the flue gas.

A further important aspect of the invention is that operating the fluidised bed combustor under superatmospheric pressure offers the possibility of increasing the pressure of the reforming reaction within the reactor tubes towards that preferred for the methanol synthesis. While such increase in reforming pressure will tend to reduce the conversion of the methane and thus increase the amount of unreacted methane in the reformate, this increase can be dealt with by diverting a part of the recycle stream of the methanol synthesis reaction back to the reformer. This will increase the heat requirement for the reforming step but since the fuel for the reformer is not provided from the feedstock, the overall feedstock conversion efficiency will not be affected. Such operation has the advantage of permitting a substantial reduction of the equipment required for cooling the hot reformate and a preferred arrangement, in which the reformate is produced at substantially the same pressure as the methanol synthesis recycle stream whereby the two may be combined for feeding to the methanol synthesis reactor, confines the primary compressor requirement to the recirculation of the methanol synthesis recycle stream thus permitting the use of large volume flow low pressure ratio compression equipment and leading to a substantial reduction in the capital cost of the plant as well as simplification of the process. A single compressor may be used for the recirculation and reformate pressurisation, if desired.

Where the fuel for the fluidised bed is an ash-containing solid, such as coal, coke, lignite, oil shale or peat, it is provided in particulate form, preferably having a maximum dimension not exceeding 6 mm, and more preferably with an average particle size of 0.25 to 1.0 mm, and is normally supplied to the bottom of the bed, the ash being removed either continuously or discontinuously. The fuel may be fed in dry powder form as or a slurry e.g. in water. Where the fuel is fusible, e.g. as in the case of oil-derived residues, it may be first melted and then fed to the fluidised bed in liquid form.

Where the fuel is ash-less or the ash formed is insufficient to form the fluidised bed, inert material may be added to provide or contribute to the formation of the fluidised bed. Any suitable inert material may be used and examples are alumina and sand. If desired, minerals such as dolomite or limestone may be included in the bed to reduce the level of oxides of sulfur in the flue gas where sulfur-containing fuels are employed. The inert material and/or limestone or dolomite should ideally have a maximum particle dimension 6 mm, and an average particle size in the range of 0.25 to 1.0 mm.

Where fuels containing high metal contents, and in particular heavy oil or oil residue fuels containing vanadium are used, it may be advantageous to introduce magnesium in the form of dolomite to suppress hot metal erosion due to vanadium, particularly in the region of the expander gas turbine.

The bed is fluidised by gas, normally the oxidant gas, e.g. air, required for the combustion, and is generally supplied from below.

In many locations, natural gas is associated with fields of solid fuel or with the recovery of crude oil and the process of the invention therefore permits the establishment of the process at a location where both the feedstock for the methanol synthesis and the fuel for providing the heat and power requirements of the process are available locally. Methane gas can also be recovered from some coal fields by established coal seam drainage techniques. In this case, any mining operations allied to the seam drainage can also be allied to the operations for obtaining the fuel. Preferably the coal is separated into a low ash fraction and a high ash fraction ("high" and "low" meaning higher and lower, respectively, than the average ash content of the coal), and the high ash fraction is employed as the fuel for the process. The low ash fraction may then be employed e.g. for metallurgical processes.

In another aspect of the invention, both the feedstock and the fuel may be provided from the by-products of oil refining. For example, the feedstock may be supplied from the gas recovered from crude oil separation and distillation and/or such operations as hydrogenation, hydrotreating, hydrocracking and cat cracking, and the fuel may be provided from the residue of atmospheric and/or vacuum distillation and/or the residues from deasphalting and/or demineralisation operations.

Figure 2:
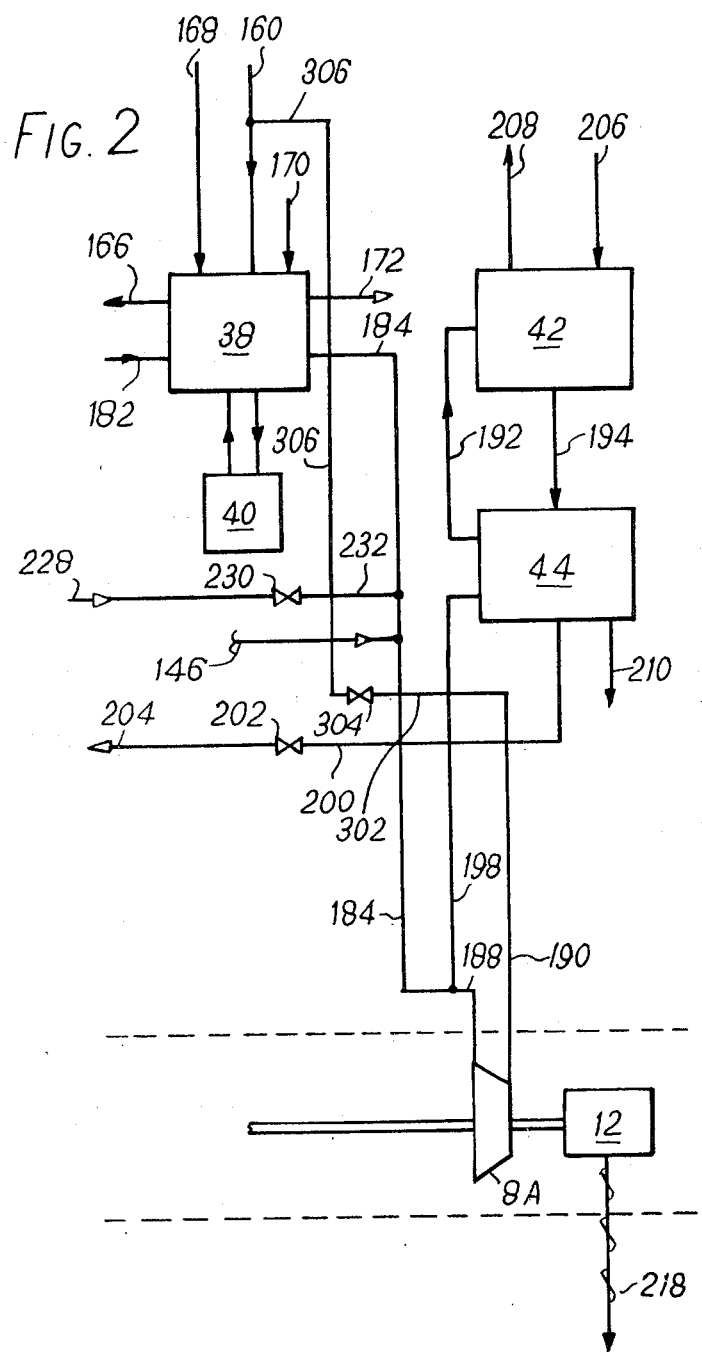

The invention is now described in greater detail with reference to preferred embodiments thereof and with the aid of the accompanying drawings in which FIG. 1 is a block flow diagram of one embodiment of the process of the invention FIG. 2 illustrates how the arrangement of FIG. 1 may be simplified when the reformate is produced at substantially the same pressure as the recycle gas from the methanol synthesis reaction, and FIG. 3 illustrates the application of the invention to a coal mining and mine gas drainage complex.

Referring to FIG. 1, 2 is a gas turbine-driven compressor and power generation unit comprising an air compressor 4 and hot gas expander 6, a synthesis gas compressor 8, a recycle compressor 10 and an alternator 12. The machine is shown in the diagram as a single fixed shaft machine but may in practice also be a single split shaft machine or a machine having more than one shaft for air compression and hot gas expansion and may also be split into a number of machines for example one machine expanding sufficient gas to drive a compressor and a separate machine or machines with gas expanders to drive the compressors 8 and 10 and the alternator 12, and in addition each compressor may be divided into separate compressors. In all cases the drive shafts to the compressors and alternator may incorporate gearboxes.

14 is a pressurised fluid bed combustor/gas reformer which includes a distribution grid 16 a fluid bed 18 and a catalyst filled reformer tube or tubes 20. 22 is a dust removal cyclone or set of cyclones or alternate filtration device; 24 and 26 are ash removal and pressure let-down devices and 28 and 29 are startup combustors. 30 is a flue gas waste heat boiler. 32 is a gas/gas heat exchanger. 34 is a carbon dioxide scrubbing system and 36 is a carbon dioxide purification and compression system. 38 is a hot synthesis gas cooling and feed gas preheating set of heat exchangers incorporating a waste heat boiler or boilers and 40 is a zinc oxide purification system.

42 is a methanol synthesis reactor which for the purposes of this description may be a catalyst filled tubular reactor in which the tubes are the heating tubes in a waste heat boiler. 44 is a gas/gas heat exchanger and reactor gas cooling and separation system and 46 is a crude methanol flash tank, treatment and distillation unit.

It should be noted that items 8, 10, 38, 40, 42, 44 and 46 comprise a hot synthesis gas fed methanol plant which may be designed in accordance with the well established principles for the design of such plants.

48 is a device or system for compressing and feeding crushed limestone and/or dolomite and/or inert material such as sand or alumina. 50 is a device or system for compressing and feeding a solid fossil fuel or fuels.

Air is drawn through duct (102) into the air compressor 4 in which it is compressed to between 5 and 40 bar, but preferably in the range between 12 and 25 bar. Intercooling during compression may be employed but aftercooling is not desirable. Compressed air passes via pipe 104 thence pipe 108, valve 110, pipe 112 and pipe 114 to the base of the fluid bed combustor 14.

For start-up, by control of valves 110 and 232 all or part of the compressed air in 104 is diverted to pipe 106 and thence via pipe 230 and valve 232 to combustor 29. Fuel at a suitable pressure is supplied via control valve 636 and pipe 234 to combustor 29 and hot combustor gases at a suitable controlled temperature pass via pipe 238 to pipe 124 and thence to the hot gas expander 6. In this manner with a suitable starter motor for the gas turbine 2 and with the compressors 8 and 10 and alternator 12 unloaded, the turbine may be started as a conventional gas turbine.

Air to start up combustor 28 passes through pipe 240 and is controlled by valve 242 and fuel at a suitable pressure in pipe 244 is controlled by a valve 246 to produce hot combusted gases in pipe 248 which pass via pipe 114 to the base of the fluid bed combustor and by control of valves 110 and 242 the partially combusted air entering the base of the fluid bed combustor 14 may be raised at a controlled rate up to a final start-up temperature in the range of 700° C. to 900° C. Alternative designs incorporating start up burners in the fluid bed 18 or in the support grid 16 are also possible.

From conveying systems 224, a solid fossil fuel, e.g. coal, lignite or solid oil residue, is fed forward at a controlled rate and under pressure by the feeding system 50. The feeding device may be a heater and pump in the case of oil residues or it may be a water slurrying device and pumping system for coal and lignite or it may be a dry powder feed system such as manufactured by Petrocarb or some suitable alternate device. The fuel from the feeding device 50 passes via pipeline 226 to the fluid fed combustor 14. The pipeline 226 may be a single line or more preferably a number of lines in parallel. The fuel is shown as fed into the fluid bed 18 above the distribution grid 16 but the feed point or points may be incorporated with the support grid 16. It is possible to feed fuel at many points in the fluid bed 18; however it is preferable to feed the fuel at least between the grid 16 and the lower manifold 180 and preferably close to the grid 16.

Inert material such as sand or alumina to produce the necessary fluid bed 18 should the fuel be relatively ash free, and/or sulphur adsorbent such as limestone or dolomite is fed via the feed duct 220 to the feeding device 48 which may be a water slurrying device and pumping system or it may be a dry powder feed synthesis such as manufactured by Petrocarb or some suitable alternate device. The inert material and/or adsorbent is fed via pipeline 222 to the fluidised bed 18 in the combustor 14. The location of the feed pipe 222 is not critical but an ideal location is above and adjacent to the grid 16. It is also possible to integrate the feeding devices 48 and 50 to feed a mixture of fuel and inert and/or adsorbent material or to slurry the inert or adsorbent material in molten oil residues.

The grid 16 may be one of a number of proprietary designs or it may be a heat resistant metal plate which may be in segmented form to allow for expansion and contraction in which a series of bubble-cap type distributors or alternate gas distribution devices are fixed. In order to ensure even distribution of air through the distributors and the bed, the distributors should have a pressure drop in the order of 0.05 to 0.10 bar.

The cross-sectional area of the bed is determined by the fluidising velocity and the volume of air required for the desired heat transfer. For any given pressure, the range of fluidising velocities in the bed for a given average particle size is well established and it is generally desirable to operate with a velocity in the lower range of available velocities in order to ensure minimum erosion of the reformer tubes 20 and manifolds and connecting lines and risers 180, 178 and 182 respectively.

The depth of the bed 18 may range from as low as 2 meters to 14 meters and possibly more. However the preferred depth for vertical cylindrical and un-finned reformer tubes is in the range of 7 to 12 meters with the tubes occupying the upper 6 to 11 meters. The fluid bed consists predominantly of ash from the fuel and/or deliberately added inert material and/or dolomite or limestone adsorbent and in order for the bed height to be held constant ash is drawn off from the bed through duct 150 to the draw-off device 26. The draw-off may be constant or intermittent and may be based on the overflowing of the bed into the duct 150 or it may be controlled by a bed level sensing device which in turn may be a device detecting the pressure drop across the bed and by inference the bed height. The draw-off device 26 draws off ash under pressure and may let it down through a system of lock-hoppers using well established designs or it may be let down through one or more rotary type valves or some alternate suitable device. Depressurised ash and/or inert material and/or spent adsorbent is discharged via duct 152.

The fluid bed is preferably of the simple up-flow type as shown in the diagram but it may also be a bed as described in the literature incorporating a spouting device and with two separate and distinct upward velocity zones.

It is preferred to operate the bed with an excess of air ranging between 20% and 50% above stoichiometric. It is possible however to operate the bed at above 50% excess air if the methanol plant is required to produce a surplus of energy in the form of mechanical energy from the turbine 2 and/or in the form of steam. It is also possible to operate the fluid bed with a deficiency of air with the combustion of carbon monoxide and possibly hydrogen formed in the bed being carried out by the addition of additional combustion air above the bed or subsequent to the combustor 14. It is generally not desirable for metallurgical reasons to operate the bed such that there are transitions between an excess and deficiency of combustion air.

The temperature of the fluid bed 18 is controlled at a fixed value and in the range of 750° to 1100° C. but more preferably within the range of 850° to 1000° C., generally by primary control of the fuel feed rate and secondary control of combustion air flow to minimise the likelihood of carbon formation in reformer tubes 20 or overheating of the connecting tube headers and risers 178 180 and 182. This temperature range also allows the use of well established alloys such as Incalloy and HK40 for tubes support etc and also the effective retention of sulphur by limestone or dolomite absorbent if sulphur removal is required.

Hot flue gases leave the combustor 14 through the duct 118. These hot gases also contain fine dust in suspension and the mixture passes through the dust removal system 22. This system may consist of cyclones and/or filtration systems but generally consists of primary and secondary cyclone systems which ensure the removal of the greater part of the entrained dust such that the maximum size of dust particle leaving the secondary cyclone should be about 10 micron so as not to unduly interfere with the operation of the hot gas expander 6. Ash is removed from separator 22 via pipe 154 to the ash discharge device 24 which may be a system of lock-hoppers and/or rotary valves or similar alternate device. Depressurised ash is removed via pipeline 156. Pressurised and cleaned hot gas from separator 22 passes via duct 120, valve 122 and ducts 124 to the turbine 6 where the gases are let down to substantially atmospheric pressure and then pass through duct 126 to a waste heat boiler 30 and thence via duct 128 to atmosphere. Suitably pressurised feed water is admitted via pipeline 130 to the boiler 30 which may incorporate a preheater and superheater and the resultant produced steam leaves via pipeline 132 for use as described below.

Methane-containing feed gas at a suitable pressure, and which preferably has been treated to remove the greater part of undesirable constituents such as hydrogen sulphide and all mercaptans, is fed at a controlled rate through pipeline 160 to the heat exchange system 38 in which it is heated to about 300° C. and thence by pipeline 162 to the zinc oxide reactor 40 in which final traces of hydrogen sulphide are removed prior to passing via pipeline 164 back to the heat exchange system 38 where a controlled amount of steam is added to the gas. The source of the steam is described below. The methane/steam mixture is heated to about 500° C. in heater 38 before passing via pipeline 166 into the pressurised combustor 14. The steam/methane mixture is then distributed by the header system 174 and a series of connecting tubes 176 (of which only one is shown) to catalyst filled reformer tubes generally indicated at 20. These tubes may be of current state of the art design i.e. vertical, cylindrical, plain tubes packed with a suitable proprietary steam reformer catalyst or they may be finned tubes or abnormally shaped tubes which would operate satisfactorily due to the reduced stresses on the tubes. The methane and any heavier hydrocarbons associated with the methane are substantially reformed to hydrogen and carbon monoxide and leave the bottom of the reformer tubes through connecting stubs 178 (only one is shown) to the bottom collection header 180 before passing up the riser 182 and thence through the shell of the combustor 14 to the heat exchange system 38. The riser 182 and the feed line 166 together with the headers 174 and 180 incorporate suitable arrangements for differential expansion and contraction due to the temperature variations during start-up, operation and shut-down of the combustor. The tubes are suitably supported using for example a high temperature metal support grid above the tubes supported from the walls of the combustor 14 using tie rods to support the upper tube header 174 the inlet pipe 166 and riser 182.

The hot reformed gases entering the heat exchange system 38 are cooled and in doing so preheat the feed gas as described above and in addition may generate steam. Suitably pressurised boiler feed water is provided to the heat exchange system 38 via pipeline 168 and steam is generated at a pressure suitable for addition to the feed gas as already described. After preheating the hot feed gas and steam mixture and generating steam as described, there is still sufficient heat in the reformate to preheat boiler feed water and generate low pressure steam at about 1.5 to 2.0 Bar before being finally cooled by cooling water or air coolers and passing via pipeline 184 to the synthesis gas compressor 8. Any additional steam for the steam reforming may be supplied, if required, via pipeline 170 and in turn this steam may be derived from pipeline 132 and/or 208 described later. Low pressure steam leaves the heat exchange system 38 via pipeline 172.

Except where $CO_2$ is present in the feed gas to the reformer, the reformate will not normally have the correct stoichiometric carbon-to-hydrogen ratio for methanol production. To rectify the deficiency, $CO_2$ is provided from the fluidised bed combustor flue gas. In order to extract carbon dioxide from the flue gas a portion of the flue gas in pipeline 120 is withdrawn via duct 134 to the heat exchanger 32 in which the flue gas is cooled to about 200° to 300° C. countercurrent to returning scrubbed gas. The cooled gas then passes via valve 136 and duct 138 to the scrubbing unit 34 which may contain a final cooler and/or direct water wash and packed limestone column to remove oxides of sulphur followed by a carbonate solution or equivalent scrubbing tower and pressure let down system for the saturated carbonate solution and a carbon dioxide separation tower or vessel. The scrubbing system 34 also includes circulating pumps and solution heat exchangers and coolers, make-up solution tanks and feed pumps and any required steam is supplied via pipeline 220. Scrubbed gas leaving 34 passes via duct 140 to the heat exchanger 32 where it is re-heated to about 800° to 850° C. prior to passing via pipeline 14 to join pipeline 124 downstream of valve 122. The quantity of carbon dioxide produced may be controlled by controlling the flow of flue gas to the scrubber 34 by control of valves 122 and 136 and/or control of the scrubbing conditions, i.e. temperature and liquid circulation rate in 34. Carbon dioxide from the scrubbing system 34 passes via pipeline 144 to the carbon dioxide compression and final purification system 36 in which the carbon dioxide is compressed to a suitable pressure and finally purified, if necessary, by suitable means such as distillation to remove traces of oxides of sulphur before passing via pipeline 146 to pipeline 184 where it is combined with cooled synthesis gas to be compressed in compressor 8. Alternatively or additionally, suitably treated carbon dioxide at suitable pressure available from any alternate source such as an ammonia plant purge may be added from pipeline 228, and the addition rate to pipeline 232 and thence to pipeline 184 being controlled by valve 230.

Reformate (with any added $CO_2$) is compressed by the compressor 8, in which intercooling may be employed, and passed via pipeline 186 to be combined with re-circulating gas from the methanol synthesis reactor in pipeline 198 before passing via pipeline 188 to the recirculation compressor 10. Compressed gas from 10 passes via pipeline 190 to the heat exchange cooling and separation system 44 in which the gas is heated prior to passing to the methanol synthesis reactor 42 via pipeline 192.

In the reactor, some of the hydrogen and oxides of carbon react to form methanol and the reaction gives off heat which boils water in the boiler surrounding the reactor tubes. Suitably pressurized feed water is added to the boiler via pipeline 206 and steam is withdrawn at up to 40 Bar from via pipeline 208. Hot reacted gas passes via pipeline 194 to the heat exchange cooling and separation system 44.

In 44 the hot reacted gases are first heat exchanged with incoming synthesis gas and then cooled by water and/or air coolers to separate out a crude water-methanol mixture which will also generaly have traces of ethers and higher alcohols. The separated liquid is bled off from the separator by a control valve to the flash tank, treatment and distillation unit 46. In 46 flash gas in the crude methanol is vented via pipeline 213 as a fuel gas or process gas stream. The crude methanol then may be treated with a small controlled amount of caustic added via pipeline 212 depending on the materials of construction of the distillation plant, and the distillation plant then removes light ethers which may be added to the vent gas in line 213, water which is removed in pipeline 214, heavy ends such as higher alcohols in pipeline 215 and product methanol which is removed via pipeline 216.

Unreacted synthesis gas leaves 44 and passes via pipeline 196 to a branch where the bulk of the gas is recycled via pipelines 198 and 188 to the recirculation compressor 10. From the branch via pipeline 200 by means of valve 202 a controlled amount of purge gas is bled from the system via pipeline 204. The purge flow is to remove unreactable components from the synthesis loop, one or more inert components such as nitrogen present in the feed gas and/or, unreformed methane present after the steam reforming reaction and/or hydrogen in excess of that required for the synthesis reaction to produce methanol. The purge gas may be used as a fuel gas or as a process gas for a separate industry e.g. ammonia manufacture or, if the methane content is high, some of the purge may be recycled back and added to the feed gas prior to pipeline 160 or the gas may be treated by one or more known techniques such as a shift reaction, scrubbing, cryogenic separation and adsorption to separate the undesirable inert components which then may be vented separately possibly as pure products, and the remaining components recycled to the process via pipeline 160 or 228 as appropriate.

The methanol plant as a whole is controlled by known and established techniques for the control of such plants and gas turbines and as an aid to control an alternator 12 is shown producing surplus power via cable 218 to that required to drive the compressors. This power may be used to drive the auxiliary units such as pumps and fans and the power produced by 12 may be adjusted to compensate for any deterioration in performance of the expander 6 between overhauls.

Alternatively 12 could be an electric motor designed to balance gas turbine/compressor assembly 2 in which case power would be supplied via cable 218.

FIG. 2 shows a modification of the arrangement of FIG. 1 suitable for use where the steam reforming step is operated at a sufficiently high pressure that the reformate in pipeline 184 is provided at substantially the same pressure as the unreacted gas in pipeline 198 from the methanol synthesis reactor 42. This method of operation permits the replacement of compressors 8 and 10 by a single recirculation compressor 8A.

The reformate in pipeline 184 is combined directly with the unreacted gas in pipeline 198 for compression in compressor 8A and subsequent feeding to the methanol synthesis reactor 42 via lines 190 and 192.

Because of the increased pressure of the reforming step, the amount of unreacted methane in line 184 is increased, possibly to as much as 10%, and a portion of the gas in pipeline 190 is withdrawn through line 302 and recycled via valve 304 and pipeline 306 to be mixed with the feed gas in 160 to the reformer.

With this arrangement the recirculation compressor 8A circulates synthesis gas through the synthesis section 42 and 44 and methane rich purge gas through the reformer system 14 and 38 and 40.

The compressor 8A has an inlet pressure of about 40 to 50 Bar and a pressure ratio of about 1.1/1.0 and may be a simple large single wheel centrifugal machine.

Referring to FIG. 3, each 402 is an underground coal seam containing high grade coking coal and a significant quantity of adsorbed methane; i.e. about 10.0 $NM^3$ of methane per ton of coal. Two such seams are shown. 404 is a mine shaft and mine, 406 is a coal washing plant. 408 is a gas compression unit 410 is a coal preparation plant, 412 is a shaft sunk for coal seam gas drainage. 414 is a gas compression unit and 416 is a methanol plant with a coal-fired pressurized fluid bed reformer as shown in FIG. 1 or in FIG. 1 as modified by FIG. 2.

Drill holes 502 are gas drainage holes drilled into the coal seam 402 in the operating mine 404 to deplete the seam of gas prior to mining. Gas is withdrawn from the coal seam at or slightly above atmospheric pressure and is collected in the manifold 504 prior to passing to the gas main 506 which passes to the above ground compressor system 408 where the gas is compressed to about 20-30 Bar or more if the methanol plant 416 is remote from the compressor 408.

Drill holes 510 are gas drainage holes drilled into the coal seams 402 in a mine drainage shaft 412 to deplete the coal seams of gas prior to mining in order to improve mine safety and/or the rate at which the coal can be ultimately mined. Gas is withdrawn from the coal seams at or above atmospheric pressure and is collected in manifolds 512 prior to passing to the gas main 514 which passes to the above ground compressor 414 where the gas is compressed to about 20-30 Bar or more if the methanol plant 416 is remote from the compressor 414.

Coal is withdrawn from the mine 404 by the hoist or conveyor 517 and passes via the conveyor 518 to the coal washery 406. In the washery, high grade low ash coal is produced and removed via the conveying system 522 as a significantly enhanced value product. Washery "middlings" and tailings are removed via conveying system 520 and thence via conveying system 526 to the coal treatment plant 410. Any excess is conveyed via 524 to dump or sale. Coal fed to 410 may contain ash in the range of 30-70% on a dry basis and may be supplemented, if necessary, by run-of-mine coal fed to 410 by conveyor 544 from the mine hoist or coveyor 517.

In the coal treatment plant 410 the coal is crushed to a suitable size range for a fluid bed combustor reformer and may provide the crushed coal in dry powder or water slurry form for conveying by the transfer pipeline, pneumatic conveyor or alternate device 528 from the treatment plant 410 to the methanol plant 416.

Feed gas to the methanol plant enters via pipeline 516 and 508 from compressors 414 and 408 respectively and sufficient drainage shafts 512 are employed to ensure a reliable and adequate supply of gas.

The methanol plant 416 operates as described before with reference to FIG. 1 or 2. Sorbent such as limestone or dolomite as required is supplied via conveying system 536; water is supplied via 532 and air is supplied via duct 530. Product methanol leaves via pipeline 538, liquid effluent such as higher alcohols via pipeline 542 and purge gases which may be used as site fuel via pipeline 546, and exhaust gas through vent 540.

The methanol may be transported by road vehicle or rail using the same mode of transport as the coal from the mine or may be pipelined if the coal transport should be by slurry pipeline. In the latter case the methanol may be either "batched" separately as methanol or as a coal slurry in the pipeline.

EXAMPLE

Using the plant described and illustrated in FIG. 1 of the drawings, methanol is generated from methane gas using the following operating conditions. The coal employed to fuel the fluid bed combustor is supplied as a slurry in water. Where the bed is pressurised, injecting water increases the power available from the flue gas and is a valuable means for disposing of waste water from processes employed in the extraction of the fuel, e.g. colliery waste water or refinery oily water waste.

| Details of steam reformer/fluid bed combustor arrangement 14 | | |
|---|---|---|
| combustors are employed, each being as follows | | |
| (A) Internal diameter of combustor | 5.8 | meters |
| (B) Depth of fluidised bed | 11.0 | meters |
| (C) Number of reformer tubes per combustor | 500 | |
| (D) Reformer tube length | 9.15 | meters |
| (E) Reformer tube outside diameter | 100 | mm |
| (F) Temperature of fluid bed | 920 | °C. |
| Details of Gas turbine assembly 2 | | |
| (G) Absorbed power of air compressor 4: | 130,000 | kW |
| (H) Absorbed power of feed gas and recirculation gas compressors 8,10: | 55,000 | kW |
| (J) Output of alternator | 25,000 | kW |

| | | | Process flow details | | |
|---|---|---|---|---|---|
| Ref | Pipeline/Vessel | Nature | Flow rate (Kg/hr) | Pressure (bar) | Temperature °C. |
| K | line 160 | Methane feed (excluding recycle) | 39,500 | 25 | 15 |
| L | *See Below | Steam to reformer | 140,040 | 25 | |
| M | Reformer tubes 20 | reforming steam/methane(including recycle methane) | 183,000 | — | 550–850 |
| N | Line 184 | reformate | 183,000 | 20 | 850 |
| O | Line 228 | $CO_2$ from external source | 36,150 | 25 | 15 |
| P | Line 146 | $CO_2$ from flue gas | nil | — | — |
| Q | Line 190/192 | Feed for methanol synthesis | — | 100 | — |
| R | Line 216 | Methanol product | 104,167 | — | — |
| S | Line 104 | Compressed Air | 725,000 | 20 | |
| T | Line 226 | Coal (as a 60/40 water/coal slurry) | 70,800 | — | — |
| W | Line 124 | HP Flue gas | 902,000 | 18 | 900 |
| X | Line 128 | LP Flue gas | 902,000 | 1.01 | 250 |

*The steam is provided from water supplied through line 168 supplemented as required by steam supplied through line 170 from lines 132 and/or 208. Total water male up to the plant in lines 130, 206 and 168 is 40,000 Kg/hr.

The coal had a calorific value of 5833 Kg Cal/Kg (Y) and was supplied in ground form with an average particle size of 0.6 mm (Z).

By way of comparison, with the same rate of supply of methane to a conventional gas-fired steam reformer in which the fuel for the reformer is provided in conventional manner from the methane, the rate of methanol production would be 64,860 Kg/hr (AA).

I claim:
1. In a method of producing methanol from a methane-containing gas by (a) steam reforming said gas at elevated temperature and superatmospheric pressure in a reaction vessel and in the presence of a catalyst to form a reformate containing hydrogen, oxides of carbon and unreacted methane and (b) subjecting a reaction stream comprising said reformate to conditions of elevated temperature and superatmospheric pressure for the formation of methanol by partial reaction of the oxides of carbon with the hydrogen in said reaction stream, the improvement comprising (c) separating the product of step (b) above into a methanol-containing stream and a recycle stream comprising unreacted hydrogen, unreacted oxides of carbon and methane; (d) recycling a first part of said recycle stream, which first part contains hydrogen and oxides of carbon, to step (b); (e) recycling a second part of said recycle stream, which second part contains methane, to step(a); (f) immersing, at least partially and for deriving the heat for the steam reforming step, said reaction vessel in a fluidized bed of finely divided solid which is heated at least in part by the combustion of a solid fossil based fuel; and (g) incorporating into said reaction stream for step (b) carbon dioxide provided from flue gas formed by the combustion of said solid, fossil based fuel.

2. A method as claimed in claim 1 in which the fluidized bed is also at superatmospheric pressure.

3. A method as claimed in claim 2 in which power is produced by expanding through an expansion engine flue gas which is recovered at superatmospheric pressure from the fluidized bed and said power is being employed to compress the oxidant gas used in the combustion of the fuel.

4. A method as claimed in claim 2 in which step (b) is effected at a higher pressure than step (a) and power is being produced by expanding through an expansion engine, flue gas which is recovered at superatmospheric pressure from the fluidized bed, said power being employed to compress the feed to step (b).

5. A method as claimed in claim 2 in which all the power required for compressing the oxidant gas and the feed to step (b) is supplied by expanding flue gas through the expansion engine.

6. A method as claimed in claim 2 in which the reformate is provided at substantially the same pressure as said first part of said recycle stream.

7. A method as claimed in claim 1 in which the solid fuel is coal and the methane-containing gas comprises gas drained from a coalfield from which the coal is supplied.

8. A method as claimed in claim 7 in which the coal is separated into a high ash fraction which is used as the solid fuel and a low ash fraction.

9. A method as claimed in claim 1 wherein the solid fuel is a solid residue obtained from refining a crude oil and the methane-containing gas comprises gas associated with the crude oil and/or produced in the refining of the crude oil.

10. A method as claimed in claim 1 in which waste water from a process employed in the extraction of the fuel is injected into the fluidized bed.

11. A method as claimed in claim 1 in which at least a part of carbon dioxide is incorporated into said reaction stream by injecting it into said methane-containing gas.

12. The method as defined in claim 1 wherein a part of the excess carbon dioxide in step (g) is provided from a supplemental source.

* * * * *